United States Patent [19]

Patel et al.

[11] Patent Number: 5,567,614

[45] Date of Patent: Oct. 22, 1996

[54] ENZYMATIC PROCESSES FOR RESOLUTION OF ENANTIOMERIC MIXTURES OF COMPOUNDS USEFUL AS INTERMEDIATES IN THE PREPARATION OF TAXANES

[75] Inventors: Ramesh N. Patel, Bridgewater; Laszlo J. Szarka, East Brunswick; Richard Partyka, Neshanic, all of N.J.

[73] Assignee: E.R. Squibb & Sons, Inc., Princeton, N.J.

[21] Appl. No.: 247,789

[22] Filed: May 23, 1994

Related U.S. Application Data

[62] Division of Ser. No. 822,015, Jan. 15, 1992, abandoned.

[51] Int. Cl.⁶ .................... C12P 17/02; C12P 17/10
[52] U.S. Cl. .................... 435/280; 435/123; 435/121; 540/357
[58] Field of Search .................... 435/280, 123, 435/121; 540/357, 510

[56] References Cited

U.S. PATENT DOCUMENTS

| | | | |
|---|---|---|---|
| 4,492,757 | 1/1985 | Kato et al. | 435/280 |
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,924,012 | 5/1990 | Colin et al. | 549/510 |
| 4,942,184 | 7/1990 | Haugwitz et al. | 514/449 |
| 4,943,528 | 7/1990 | Nakamura et al. | 435/158 |
| 4,960,790 | 10/1990 | Stella et al. | 514/449 |
| 5,015,744 | 5/1991 | Holton et al. | 549/510 |
| 5,254,580 | 10/1993 | Chen et al. | 514/449 |
| 5,272,171 | 12/1993 | Ueda et al. | 514/449 |
| 5,294,637 | 3/1994 | Chen et al. | 514/449 |
| 5,300,638 | 4/1994 | Farina et al. | 540/357 |

FOREIGN PATENT DOCUMENTS

| | | |
|---|---|---|
| 336841 | 10/1989 | European Pat. Off. |
| 400971 | 12/1990 | European Pat. Off. |
| 404586 | 12/1990 | European Pat. Off. |
| 405104 | 1/1991 | European Pat. Off. |
| 414610 | 2/1991 | European Pat. Off. |
| 421283 | 4/1991 | European Pat. Off. |
| 428376 | 5/1991 | European Pat. Off. |
| 529483 | 3/1993 | European Pat. Off. |
| 534707 | 3/1993 | European Pat. Off. |
| 534708 | 3/1993 | European Pat. Off. |
| 534709 | 3/1993 | European Pat. Off. |
| 552041 | 7/1993 | European Pat. Off. |
| 558959 | 9/1993 | European Pat. Off. |
| 582469 | 2/1994 | European Pat. Off. |
| 604910 | 7/1994 | European Pat. Off. |

OTHER PUBLICATIONS

Nagai et al., Chem, Pharm. Bull. 40(8), 1992 pp. 2227–2229.

Wintherup et al., "Taxus spp. Needles Contain Amounts of Taxol Comparable to the Bark of *Taxus brevifolia*: Analysis and Isolation", *J. of Natural Products*, 53, No. 5, pp. 1249–1255 (Sep.–Oct. 1990).

Senilh et al., "Mise en evidence de nouveaux analogues du taxol extraits de Taxus baccata", *J. of Nat. Products*, 47, No. 1, pp. 131–137 (Jan.–Feb. 1984) (abstract in English).

Denis et al., "A Highly Efficient, Practical Approach to Natural Taxol", *J. Am. Chem. Soc.*, 110, pp. 5917–5919 (1988).

Magri et al., "Modified Taxols. 3. Preparation and Acylation of Baccatin III", *J. Org. Chem.*, 51, pp. 3239–3242 (1986).

Honig et al., "Chemo–Enzymatic Synthesis of All Isomeric 3–Phenylserines and –Isoserines", *Tetrahedron*, 46, No. 11, pp. 3841–3850 (1990).

Fones, "The Isomers of the β–Phenylserines", *J. Biol. Chem.*, 204, pp. 323–328 (1953).

Denis et al., "An Efficient, Enantioselective Synthesis of the Taxol Side Chain," *J. Org. Chem.*, 51, pp. 46–50 (1986).

Chemical Abstracts 114: 9448h; Search for new anticancer substances, Guenard et al., *Recherche*, 21, (226), pp. 1427–1429 (1990) (abstract only).

Chemical Abstracts 109: 129360r; A synthesis of taxusin, Holton et al., *J. Am. Chem. Soc.*, 110 (19), pp. 6558–60 (1988) (abstract only).

Chemical Abstracts 112(13) 119169h; Application of the vicinal hydroxyamination reaction with asymmetric induction to the hemisynthesis of taxol and analogs; Mangatal et al. (1989) (abstract only).

Cooper et al., "Chiral control of the Staudinger reaction," *Pure & Appl. Chem.*, 59, No. 3, pp. 485–492 (1987).

Borer et al., "An Asymmetric Synthesis of a 3–Hydroxy–βLactam by Ketene–Imine Cycloaddition: Utilization of Chiral Ketenes from Carbohydrates," *Tetrahedron Letters*, 32, No. 8, pp. 1039–1040 (1991).

Barton et al., "Asymmetric Synthesis of 1, 3, 4–Trisubstituted and 3, 4–Disubstituted 2–Azetidionones: Strategy Based on the Use of D–Glucosamine as a Chiral Auxillary in the Staudinger Reaction," *J. Chem. Soc. Perkin Trans I*, pp. 3211–3212 (1990).

Abdel–Magid et al., "Metal—Assisted Aldol Condensation of Chiral α–Halogenated Imide Enolates: A Stereocontrolled Chiral Epoxide Synthesis," *J. Am. Chem. Soc.*, 108, pp. 4595–4602 (1986).

Parness et al., "Structure–Activity Study of Cytotoxicity and Microtubule Assembly In vitro by Taxol and Related Taxanes," *Biochemical and Biophysical Research Communications*, 105, No. 3, pp. 1082–1089 (1982).

Denis et al., "An Improved Synthesis of the Taxol Side Chain and of RP 56976," *J. Org. Chem.*, 55, pp. 1957–1959 (1990).

(List continued on next page.)

*Primary Examiner*—Irene Marx
*Attorney, Agent, or Firm*—Suzanne E. Babajko

[57] ABSTRACT

Methods for the enzymatic resolution of mixtures of enantiomers, such as β-lactam compounds, which may be employed as intermediates in the preparation of taxanes such as taxol, the latter useful in the pharmaceutical field.

31 Claims, No Drawings

OTHER PUBLICATIONS

Ojima et al., "Efficient and Practical Asymmetric Synthesis of the Taxol C-13 Side Chain, N-Benzoyl-(2R, 3S)-3-phenylisoserine, and Its Analogues via chiral 3-Hydroxy-4-aryl-β-lactams through Chiral Ester Enolate -Imine Cyclocondensation," *J. Org. Chem.*, 56, pp. 1681–1683 (1991).

Gueritte-Voegelein, "Chemical Studies of 10-Deacetyl Baccatin III. Hemisynthesis of Taxol Derivatives," *Tetrahedron*, 42, No. 16, pp. 4451–4460 (1986).

Laschat et al., "Carbohydrates as Chiral Templates: Stereoselective synthesis of (R)-Homoallyl Amines Using L-Fucose as the Auxillary Formally Enantiomeric to D-Galactose," *Synlett*, pp. 629–630 (Oct. 1990).

Senilh et al., "Hemisynthese de nouveaux analogues du taxol. Etude de leur interaction avec la tubuline," *C.R. Acad. Sc. Paris*, Serie II, No. 15, pp. 1039–1043 (1984).

Georg et al., "Asymmetric Synthesis of α-Alkylated α-Amino Acids: Azocane-2-Carboxylic Acids", *Tetrahedron Letters*, 33, No. 1, pp. 17–20 (1992).

Georg et al., "Stereoselective Syn Aldol Reaction of the Lithium Ester Enolate of Ethyl N,N-Dimethylglycine in the Presence of Triethylborane," *Tetrahedron Letters*, 32, No. 40, pp. 5521–5524 (1991).

Georg et al., "Asymmetric Synthesis of β-Lactams and N-Benzoyl-3-Phenylisoserines via the Staudinger Reaction," *Tetrahedron Letters*, 32, No. 27, pp. 3151–3154 (1991), plus Correction (1 page).

Georg et al., "An Improved Method for the Stereoselective Synthesis of β-Lactams from Carboxylic Acids and Imines," *Tetrahedrom Letters*, 32, No. 5, pp. 581–584 (1991).

Hoenig, et al., "Chemoenzymic syntheses of enantiomerically pure hydroxy amino acids", Chemical Abstracts, vol. 115, No. 17, 28 Oct. 1991, Columbus, Ohio, US; abstract No. 183831g, p. 985.

Kozo, et al., "Optically active threo—3—phenylserine derivatives", Chemical Abstracts, vol. 105, No. 3, 21 Jul. 1986, Columbus, Ohio, US, abstract No. 23102k, p. 537 (JP-A-60 248 192; 7 Dec. 1985).

Palomo, et al., "Highly Stereoselective Synthesis of α-Hydroxy β-Amino acids through β—Lactams: Application to the Synthesis of the Taxol and Bestatin Side Chains and Related Systems", Tetrahedron Letters, vol. 31, No. 44, 1990, Oxford GB, pp. 6429–6432.

Dordick, Biotechnol. Prog., 8:259–67 (1992).

Gou et al., J. Org. Chem., 58, 1287–1289 (1993).

Iriuchijima et al., Agric. Biol. Chem., 45:1389–92 (1981).

Kato et al., Tetrahedron Letters, 28:1303–1306 (1987).

Langrand et al., "Lipase Catalyzed Reactions and Strategy for Alcohol Resolution", Tetrahedron Letters, vol. 27, No. 1, pp. 29–32 (1986).

Ojima e al., Tetrahedron, vol. 48, no. 34, pp. 6985–7012 (1992).

Ojima et al., Tetrahedron Lett., vol. 33, No. 39, pp. 5737–5740 (1992).

Parida et al., J. Am. Chem. Soc., 113:2253–59 (1991).

Sonnet et al., Lipids, 26:295–300 (1991).

Yamazaki et al., Bioorg. & Med. Chem. Lett., 1:271–6 (1991).

Jones, Tetrahedron, 42: 3351–3403 (1986).

Honig et al., Amino Acids: Chem. Biol. Med., 134–42 (1989).

Brieva et al., J. Org. Chem., 58: 1068–1075 (1993).

Okumura et al., BBA, 575: 156–165 (1979).

Hills et al., BBA, 1042: 237–240 (1990).

ENZYMATIC PROCESSES FOR RESOLUTION OF ENANTIOMERIC MIXTURES OF COMPOUNDS USEFUL AS INTERMEDIATES IN THE PREPARATION OF TAXANES

This is a division of application Ser. No. 07/822,015, filed Jan. 15, 1992 now abandoned.

FIELD OF THE INVENTION

The present invention relates to enzymatic processes for the resolution of enantiomeric mixtures of compounds useful as intermediates in the preparation of taxanes, particularly taxol and taxol derivatives, the latter compounds finding utility in the pharmaceutical field.

BACKGROUND OF THE INVENTION

Taxanes are diterpene compounds which find utility in the pharmaceutical field. For example, taxol, a taxane having the structure:

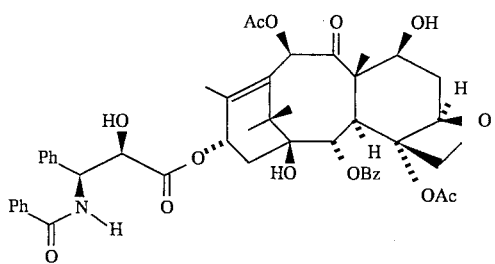

where Ph is phenyl, Ac is acetyl and Bz is benzoyl has been found to be an effective anticancer agent, particularly useful in the treatment of ovarian cancer.

Naturally occurring taxanes such as taxol may be found in plant materials, and have been isolated therefrom. Such taxanes may, however, be present in plant materials in relatively small amounts so that, in the case of taxol, for example, large numbers of the slow-growing yew trees forming a source for the compound may be required. The art has thus continued to search for synthetic, including semi-synthetic routes for the preparation of naturally occurring taxanes such as taxol, as well as routes for the preparation of synthetic, pharmaceutically useful analogs thereof.

As the stereochemistry of these compounds may affect their pharmaceutical activity, methods allowing efficient stereospecific preparation of intermediates as well as the final taxane products are particularly sought.

SUMMARY OF THE INVENTION

The present invention provides efficient methods for the resolution of enantiomeric mixtures, preferably racemic mixtures, of compounds useful as intermediates in the preparation of taxanes such as taxol, and thus for the stereospecific preparation of these compounds.

Specifically, the present invention provides a method for the resolution of a mixture I comprising the enantiomers Ia and Ib, where $R^1$ is in the cis position relative to $R^2$ in both Ia and Ib, or where $R^1$ is in the trans position relative to $R^2$ in both Ia and Ib:

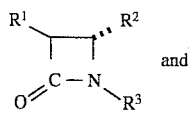

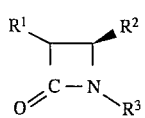

where $R^1$ is hydroxyl; halo;

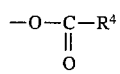

where $R^4$ is alkyl, alkenyl, alkynyl, aryl, cycloalkyl, cycloalkenyl or hetero;

$R^2$ is aryl; alkyl; alkenyl; or alkynl; and $R^3$ is hydrogen; $R^4$;

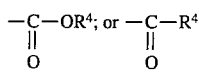

where $R^4$ is independently selected from those groups recited for $R^4$ above; comprising the step of contacting said mixture I with an enzyme or microorganism capable of catalyzing the stereoselective conversion of one of said compounds Ia or Ib to a non-enantiomeric form, and effecting said conversion.

The present invention also provides a process for the resolution of a mixture IV comprising the enantiomers IVa and IVb:

and

where $T^a$ is

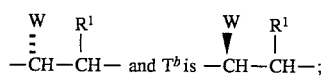

or $T^a$ is

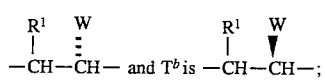

where $R^1$ is in the erythro position relative to the group W in both IVa and IVb, or where $R^1$ is in the threo position relative to the group W in both IVa and IVb;

W is $-NHR^3$ or $-N_3$;

$R^1$ is hydroxyl; halo; or

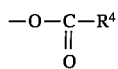

where
$R^4$ is alkyl, alkenyl, alkynyl, aryl, cycloalkyl, cycloalkenyl or hetero;

$R^2$ is aryl; alkyl; alkenyl; or alkynyl;

$R^3$ is hydrogen; ; $R^4$;

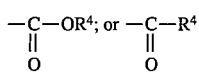

where $R^4$ is independently selected from those groups recited for $R^4$ above; and $R^6$ is hydrogen; or $R^4$ where $R^4$ is independently selected from those groups recited for $R^4$ above;

comprising the step of contacting said mixture IV with an enzyme or microorganism capable of catalyzing the stereoselective conversion of one of said compounds IVa or IVb to a non-enantiomeric form, and effecting said conversion.

Exemplary embodiments for the aforementioned stereoselective conversions include stereoselective hydrolysis, stereoselective esterification, stereoselective transesterification and stereoselective dehalogenation, particularly stereoselective hydrolysis or esterification.

Groups, such as hydroxyl groups, on the compounds of formulae I or IV may optionally be protected for use in the resolution methods of the present invention; such groups may optionally be subsequently deprotected.

DETAILED DESCRIPTION OF THE INVENTION

The methods of the present invention are described further as follows.

Cis Enantiomers

The following pair of cis enantiomers may be separated by the enzymatic methods of the instant invention:

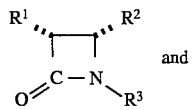 (Ia(1))

and

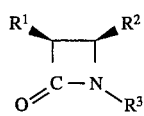 (Ib(1))

that is, enantiomers Ia and Ib where $R^1$ is in the cis position relative to $R^2$ in both Ia and Ib.

It is preferred to resolve a mixture of cis enantiomers as described above according to the methods of the instant invention.

Trans Enantiomers

The following pair of trans enantiomers may be separated by the enzymatic methods of the instant invention:

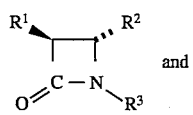 (Ia(2))

and

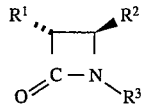 (Ib(2))

that is, enantiomers I a and Ib where $R^1$ is in the trans position relative to $R^2$ in both I a and Ib.

Erythro Enantiomers

The following pairs of erythro enantiomers may be separated by the enzymatic methods of the instant invention:

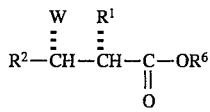 (IVa(1))

and

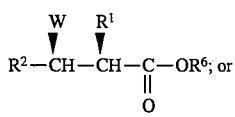 (IVb(1))

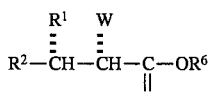 (IVa(2))

and

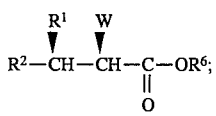 (IVb(2))

that is, enantiomers IVa and IVb where $R^1$ is in the erythro position relative to the group W in both IVa and IVb.

Threo Enantiomers

The following pairs of threo enantiomers may be separated by the enzymatic methods of the instant invention:

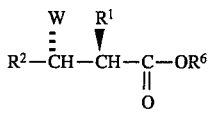 (IVa(3))

and

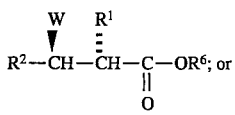 (IVb(3))

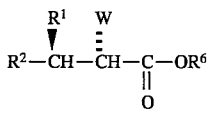 (IVa(4))

and

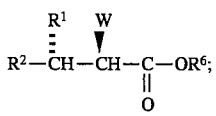 (IVb(4))

that is, enantiomers IVa and IVb where $R^1$ is in the threo position relative to the group W in both IVa and IVb.

Preferred Methods for the Resolution of Mixture I

Mixture I, comprising an enantiomeric mixture of β-lactams Ia and Ib, is preferably resolved by stereoselective hydrolysis, esterification or dehalogenation. A particularly preferred method for the resolution of a mixture I comprising the enantiomers Ia(1) and Ib(1):

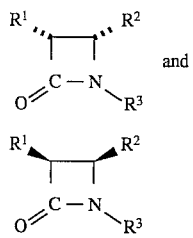
(Ia(1))

and

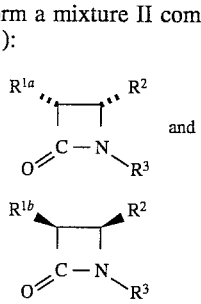
(Ib(1))

to form a mixture II comprising the compounds IIa(1) and IIb(1):

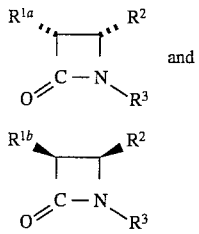
(IIa(1))

and (IIb(1))

where
$R^2$ is aryl; alkyl; alkenyl; or alkynyl; and
$R^3$ is hydrogen; $R^4$;

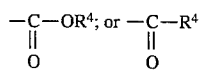

where $R^4$ is alkyl, alkenyl, alkynyl, aryl, cycloalkyl, cycloalkenyl or hetero;
comprises one of the following steps (i), (ii), or (iii):
(i) where
$R^1$ is

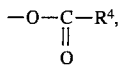

where $R^4$ is independently selected from those groups recited for $R^4$ above; and
one of $R^{1a}$ or $R^{1b}$ is the same as $R^1$ and the other of $R^{1a}$ or $R^{1b}$ is hydroxyl;
the step of contacting said mixture I, in the presence of water and/or an organic alcohol, with an enzyme or microorganism capable of catalyzing the stereoselective hydrolysis of mixture I to provide said mixture II; or
(ii) where
$R^1$ is hydroxyl; and
one of $R^{1a}$ or $R^{1b}$ is hydroxyl and the other of $R^{1a}$ or $R^{1b}$ is

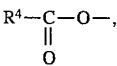

where $R^4$ is independently selected from those groups recited for $R^4$ above;
the step of contacting said mixture I, in the presence of a compound III:

(III)

where $R^4$ is as defined above for $R^{1a}$ or $R^{1b}$ and L is a leaving group, with an enzyme or microorganism capable of catalyzing the stereoselective esterification of mixture I to provide said mixture II; or
(iii) where
$R^1$ is a halogen atom; and
one of $R^{1a}$ or $R^{1b}$ is halogen and the other of $R^{1a}$ or $R^{1b}$ is hydroxyl;
the step of contacting said mixture I, in the presence of a hydroxide ion donor, with an enzyme or microorganism capable of catalyzing the stereoselective dehalogenation of mixture I to provide said mixture II.

The above methods may be employed in the resolution of other enantiomeric mixtures of the instant invention, although resolution of the above cis enantiomers Ia(1) and Ib(1) is preferred.

Preferred Methods for the Resolution of Mixture IV

Mixture IV is preferably resolved by stereoselective hydrolysis, esterification, dehalogenation or transesterification. A particularly preferred method for the resolution of a mixture IV comprising the enantiomers IVa(1) and IVb(1):

(IVa(1))

and

(IVb(1))

to form a mixture V comprising compounds Va(1) and Vb(1):

(Va(1))

and

(Vb(1))

where
$R^2$ is aryl; alkyl; alkenyl; or alkynyl;
$R^3$ is hydrogen; $R^4$;

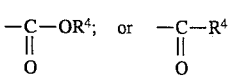

where $R^4$ is alkyl, alkenyl, alkynyl, aryl, cycloalkyl, cycloalkenyl or hetero; and
$R^6$ is hydrogen; or $R^4$ where $R^4$ is independently selected from those groups recited for $R^4$ above;
comprises one of the following steps (i), (ii), or (iii):
(i) where
$R^1$ is

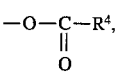

where $R^4$ is independently selected from those groups recited for $R^4$ above; and one of $R^{1a}$ or $R^{1b}$ is the same as $R^1$ and the other of $R^{1a}$ or $R^{1b}$ is hydroxyl; the step of contacting said mixture IV, in the presence of water and/or an organic alcohol, with an enzyme or microorganism capable of catalyzing the stereoselective hydrolysis of mixture IV to provide said mixture V; or (ii) where $R^1$ is hydroxyl; and one of $R^{1a}$ or $R^{1b}$ is hydroxyl and the other of $R^{1a}$ or $R^{1b}$ is

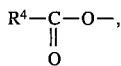, where is independently selected from those groups recited for $R^4$ above;

the step of contacting said mixture IV, in the presence of a compound III:

 (III)

where $R^4$ is as defined above for $R^{1a}$ or $R^{1b}$ and L is a leaving group, with an enzyme or microorganism capable of catalyzing the stereoselective esterification of mixture IV to provide said mixture V; or (iii) where $R^1$ is a halogen atom; and one of $R^{1a}$ or $R^{1b}$ is halogen and the other of $R^{1a}$ or $R^{1b}$ is hydroxyl;

the step of contacting said mixture IV, in the presence of a hydroxide ion donor, with an enzyme or microorganism capable of catalyzing the stereoselective dehalogenation of mixture IV to provide said mixture V.

A further particularly preferred method for the resolution of a mixture IV comprising the enantiomers IVa(1) and IVb(1):

and

to form a mixture VI comprising compounds VIa(1) and VIb(1):

and

where $R^1$ is hydroxyl; halo; or

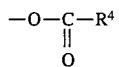

where $R^4$ is alkyl, alkenyl, alkynyl, aryl, cycloalkyl, cyloalkenyl or hetero;

$R^2$ is aryl; alkyl; alkenyl; or alkynyl; and $R^3$ is hydrogen; $R^4$;

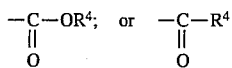

where $R^4$ is independently selected from those groups recited for $R^4$ above;

comprises one of the following steps (i), (ii), or (iii):

(i) where $R^6$ is hydrogen; and one of $R^{6a}$ or $R^{6b}$ is hydrogen and the other of $R^{6a}$ or $R^{6b}$ is $R^4$ where $R^4$ is independently selected from those groups recited for $R^4$ above;

the step of contacting said mixture IV, in the presence of an organic alcohol of the formula VII:

$R^4$—OH (VII)

where $R^4$ is as defined above for $R^{6a}$ or $R^{6b}$, with an enzyme or microorganism capable of catalyzing the stereoselective esterification of mixture IV to provide said mixture VI; or (ii) where $R^6$ is $R^4$ where $R^4$ is independently selected from those groups recited for $R^4$ above; and one of $R^{6a}$ or $R^{6b}$ is the same as $R^6$ and the other of $R^{6a}$ or $R^{6b}$ is hydrogen;

the step of contacting said mixture IV, in the presence of water, with an enzyme or microorganism capable of catalyzing the stereoselective hydrolysis of mixture IV to provide said mixture VI; or (iii) where $R^6$ is $R^4$ where $R^4$ is independently selected from those groups recited for $R^4$ above; and one of $R^{6a}$ or $R^{6b}$ is the same as $R^6$ and the other of $R^{6a}$ or $R^{6b}$ is $R^7$, where $R^7$ is alkyl, alkenyl, alkynyl, aryl, cycloalkyl, cycloalkenyl or hetero, except that $R^7$ is not the same as $R^6$;

the step of contacting said mixture IV, in the presence of an organic alcohol of the formula VIII:

$R^7$—OH (VIII)

where $R^7$ is as defined above, with an enzyme or microorganism capable of catalyzing the stereoselective transesterification of mixture IV to provide said mixture VI.

The above methods may be employed in the resolution of other enantiomeric mixtures of the instant invention, although resolution of the above enantiomers IVa(1) and IVb(1) is preferred.

The compound pairs so prepared, such as IIa(1) and IIb(1), are non-enantiomeric and may subsequently be separated to yield optically active, preferably optically pure, compounds. An optical purity greater than 99%, particularly 99.5%, is preferred.

The instant invention also provides a compound of the mixture I or IV substantially free of other isomers, which compound may be prepared by the methods of the invention.

Definitions

The term "stereoselective conversion", as used herein, refers to the preferential reaction of one enantiomer relative to another, that is, asymmetric, enantioselective, reaction. Likewise, the terms "stereoselective hydrolysis", "stereoselective esterification", "stereoselective dehalogenation" and "stereoselective transesterification" refer to the preferential hydrolysis, esterification, dehalogenation and transesterification, respectively, of one enantiomer relative to another.

The term "mixture", as said term is used herein in relation to enantiomeric compounds, denotes mixtures having equal (racemic) or non-equal amounts of enantiomers.

The term "resolution" as used herein denotes partial, as well as, preferably, complete resolution.

The term "non-enantiomeric form" as used herein denotes the structure of a compound, originally one of an enantiomeric pair, in which at least one group has been modified so that said compound is no longer the mirror image of the other compound of the original enantiomeric pair.

The terms "enzymatic process" or "enzymatic method" as used herein denote a process or method of the present invention employing an enzyme or microorganism.

The terms "alkyl", "alkan" or "alk" as employed herein alone or as part of another group preferably denote both straight and branched chain, optionally substituted hydrocarbons containing 1 to 15 carbons in the normal chain, preferably 1 to 6 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Exemplary substituents may include one or more groups selected from the following: halo (especially chloro), trihalomethyl, alkoxy (for example, where two alkoxy substituents form an acetal), aryl such as unsubstituted aryl, alkyl-aryl or haloaryl, cycloalkyl such as unsubstituted cycloalkyl or alkyl-cycloalkyl, hydroxy or protected hydroxy, carboxyl, alkyloxycarbonyl, alkylamino, alkylcarbonylamino, amino, arylcarbonylamino, nitro, cyano, thiol or alkylthio. Particularly preferred alkyl substituents are hydroxyl groups.

The term "alkenyl" as employed herein alone or as part of another group preferably denotes such optionally substituted groups as described above for alkyl, further containing at least one carbon to carbon double bond.

The term "alkynyl" as employed herein alone or as part of another group preferably denotes such optionally substituted groups described above for alkyl, further containing at least one carbon to carbon triple bond.

The term "cycloalkyl" as employed herein alone or as part of another group preferably denotes optionally substituted saturated cyclic hydrocarbon groups containing one to three rings and 3 to 12 ring carbons, preferably 3 to 8 ring carbons, which include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "cycloalkenyl" as employed herein alone or as part of another group preferably denotes such optionally substituted groups as described above for cycloalkyl, further containing at least one carbon to carbon double bond in the ring system.

The terms "aryl" or "ar" as employed herein preferably denote monocyclic or bicyclic substituted or unsubstituted aromatic groups containing from 6 to 12 carbons in the ring portion, such as phenyl, biphenyl, naphthyl, substituted phenyl, substituted biphenyl or substituted naphthyl. Exemplary substituents (preferably three or fewer) include one or more of the following groups: alkyl such as unsubstituted alkyl, haloalkyl, or cycloalkylalkyl, halogen, alkoxy such as unsubstituted alkoxy or haloalkoxy, hydroxy, aryl such as phenyl or halophenyl, aryloxy such as phenoxy, $R^4$-carbonyloxy, where $R^4$ is as defined above, such as alkylcarbonyloxy or benzoyloxy, allyl, cycloalkyl, alkylamino, dialkylamino, amido such as alkylcarbonylamino or arylcarbonylamino, amino, nitro, cyano, alkenyl, thiol, $R^4$-carbonyl, where $R^4$ is as defined above, or methylenedioxy where the methylene group may be substituted by 1 or 2 lower alkyl groups, 1, 2 or 3 arylalkenyl groups, and/or 1, 2 or 3 alkylthio groups. Particularly preferred aryl groups are phenyl and substituted phenyl, especially phenyl substituted by one or more hydroxyl, alkyl and/or alkoxy groups such as p-methoxyphenyl, o-methoxyphenyl, p-hydroxyphenyl, o-hydroxyphenyl and m-hydroxyphenyl.

The term "halogen" or "halo" as used herein refers to chlorine, bromine, fluorine, and iodine, with chlorine or fluorine being preferred.

The term "heterocyclo" preferably denotes optionally substituted fully saturated or unsaturated, monocyclic or bicyclic, aromatic or non-aromatic hydrocarbon groups having 5 or 6 atoms in each ring and at least one heteroatom in at least one ring. The heterocyclo group preferably has 1 or 2 oxygen atoms, 1 or 2 sulfur atoms, and/or 1 to 4 nitrogen atoms in the ring. Exemplary substituents include halogen(s), 1, 2 or 3 $C_{1-6}$ alkoxy groups, 1, 2 or 3 hydroxy groups, 1, 2 or 3 phenyl groups, 1, 2 or 3 alkanoyloxy groups, 1, 2 or 3 benzoyloxy groups, 1, 2 or 3 halophenyl groups, 1, 2 or 3 alkyl groups such as 1, 2, or 3 aralkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2, or 3 cyano groups, and 1, 2 or 3 thiol groups. Exemplary heterocyclo groups are 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, 2-, 3- and 4-azepinyl, 4-, 5-, 6- and 7-indolyl, 4-, 5-, 6- and 7-isoindolyl, 5-, 6-, 7- and 8-quinolinyl, 5-, 6-, 7- and 8-isoquinolinyl, 4-, 5-, 6-, and 7-benzothiazolyl, 4-, 5-, 6- and 7-benzoxazolyl, 4-, 5-, 6- and 7-benzimidazolyl, 4-, 5-, 6- and 7-benzoxadiazolyl, and 4-, 5-, 6- and 7-benzofurazanyl.

The term "hydroxyl protecting group" as used herein denotes a group capable of protecting a free hydroxyl group which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fiser & Fiser. Exemplary hydroxyl protecting groups include methoxymethyl, 1-ethoxyethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

Starting Materials

A mixture I starting material comprising β-lactam compounds Ia and Ib may be prepared by methods known to the skilled artisan, such as those described in European Patent Application No. 400,971, incorporated herein by reference. For example, a racemic mixture of cis-β-lactam compounds Ia and Ib may be prepared by the formation of an imine of the formula:

$$R^2-CH=N-R^3$$

by reaction of an aldehyde of the formula:

$$R^2-CHO$$

such as benzaldehyde, with an amine derivative of the formula:

$$H_2N-R^3$$

such as p-methoxyaniline.

The imine so prepared may then be reacted with an acyl chloride of the formula:

$$R^1-CH_2-\overset{\overset{O}{\|}}{C}-Cl$$

such as α-acetoxy acetyl chloride, to produce a racemic mixture of cis-β-lactam compounds of the formulae Ia and Ib. This latter reaction may be conducted in the presence of a base such as triethylamine in a solvent such as methylene chloride at a temperature such as $-20°$ C., followed by warming to $25°$ C.

The above procedure may, in turn, be followed by modification of the lactam formed, should a different lactam starting material be desired. For example, a cis-1-p-methoxyphenyl- 3-acetoxy-4-phenylazetidin-2-one racemate prepared as above, in acetonitrile at a temperature such as $-10°$ C. to $-5°$ C., may be treated with a solution of ceric ammonium nitrate in water to yield a cis-3-acetoxy-4-phenylazetidin-2-one racemate. The latter compound may, for example, further be hydrolyzed, e.g., with aqueous potassium hydroxide, to yield cis-3-hydroxy-4-phenylazetidin- 2-one.

A mixture IV starting material comprising a racemate of compounds IVa and IVb may be prepared by methods known to the skilled artisan.

Starting mixtures which are other than racemic may be obtained, for example, by addition of one of the compounds Ia or Ib to a racemic mixture I, or by addition of one of the compounds IVa or IVb to a racemic mixture IV, in other than equal portions.

The starting mixtures I or IV may contain, for example, the diastereomers of the compounds Ia and Ib or IVa and IVb, although it is preferred that such compounds are separated prior to conducting the enzymatic resolution methods of the present invention.

Preferred Compounds

Cis compounds of the formula I have a stereoisomeric configuration which is preferred in compounds employed as intermediates in the preparation of taxanes such as taxol. Compounds of the mixtures I and II having the same absolute configuration corresponding to that of a compound Ia where $R^1$ is acetyloxy, $R^2$ is phenyl and $R^3$ is hydrogen in the 3R,4S configuration are particularly preferred.

Erythro compounds of the formula IV have a stereoisomeric configuration which is preferred in compounds employed as intermediates in the preparation of taxanes such as taxol. Compounds of the mixtures IV, V and VI having the same absolute configuration corresponding to that of a compound IVa(1) where $R^1$ is hydrogen, $R^2$ is phenyl, W is —NHR$^3$ and $R^3$ is hydrogen, and $R^6$ is hydrogen in the 2R,3S configuration are preferred. In mixture IV,

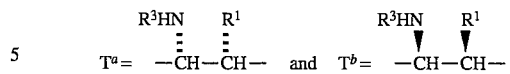

is preferred.

Resolution of β-lactams of the formula I is preferred.

In the compounds of the present invention, $R^1$ is preferably alkanoyloxy, such as unsubstituted alkanoyloxy (e.g., acetyloxy) or chloroalkanoyloxy (e.g chloroacetyloxy), or hydroxy; $R^2$ is preferably phenyl or substituted phenyl; and $R^3$ is preferably hydrogen, phenyl, substituted phenyl such as methoxyphenyl or hydroxyphenyl, phenylcarbonyl, substituted phenylcarbonyl, alkylcarbonyl, alkenylcarbonyl or alkoxycarbonyl such as t-butoxycarbonyl. $R^6$ may be hydrogen or $R^4$ the latter forming an ester group. $R^6$ is preferably hydrogen or a $C_{1-6}$ alkyl such as methyl.

Enzymes and Microorganisms

The enzyme or microorganism employed in the methods of the present invention may be any enzyme or microorganism having the ability to catalyze the stereoselective conversions as described herein. Various enzymes, such as esterases, lipases and proteases, regardless of origin or purity, are suitable for use in the present invention. The enzyme may, for example, be in the form of animal or plant enzymes or mixtures thereof, cells of microorganisms, crushed cells, extracts of cells, or of synthetic origin.

With respect to the use of microorganisms, the methods of the present invention may be carried out using any microbial cellular material having the ability to catalyze the stereoselective conversions as described herein. The cells may be used in the form of intact wet cells or dried cells such lyophilized, spray-dried or heat-dried cells. Cells may also be used in the form of treated cell material such as ruptured cells or cell extract. The cells or cellular materials may be employed in the free state or immobilized on a support such as by physical adsorption or entrapment.

Exemplary genera of microorganisms suitable as sources of catalyzing enzymes include Mucor, Escherichia, Staphylococcus, Agrobacterium, Acinetobacter, Rhizopus, Aspergillus, Nocardia, Streptomyces, Trichoderma, Candida, Rhodotorula, Torulopsis, Proteus, Bacillus, Alcaligenes, Pseudomonas, Rhodococcus, Brevibacterium, Geotrichum, Enterobacter, Chromobacterium, Arthrobacter, Microbacterium, Mycobacterium, SaccharomUces, Penicillium, Methanobacterium, Botrytis, Chaetomium, Ophiobolus, Cladosporium and the like. The use of genetically engineered host cells is also contemplated.

Specific microorganisms suitable for use in the present processes include *Chromobacterium viscosum, Pseudomonas aeuriginosa* such as ATCC 25619, *Pseudomonas fluorescens, Pseudomonas putida* such as ATCC 31303, *Pseudomonas ovalis, Escherichia coli, Staphylococcus aureus, Alcaligenes faecalis, Streptomyces griseus, Pseudomonas cepacia, Candida rugosa* such as ATCC 14830, *Geotrichum candidum* such as ATCC 32345, *Streptomyces clavuligerus, Nocardia erthropolis, Nocardia asteraides, Mycobacterium phlei, Agrobacterium radiobacter, Aspergillus niger, Rhizopus oryzae* and the like. Two or more, as well as a single, species of microorganism may be employed when carrying out the instant processes. The term "ATCC" as used herein refers to the accession number of the American Type Culture Collection, 12301 Parklawn Drive, Rockville, Md. 20852, the depository for the organism referred to.

The resolution methods of the instant invention may be carried out subsequent to the growth of the microorganism(s) employed, or concurrently therewith that is, in the latter case, by in situ fermentation and resolution. The growth of microorganisms may be achieved by the skilled artisan, for example, by the use of an appropriate medium containing nutrients such as carbon and nitrogen sources and trace elements.

Exemplary, commercially available enzymes suitable for use in the present invention include lipases such as Amano PS-30 (*Pseudomonas cepacia*), Amano GC-20 (*Geotrichum candidum*), Amano APF (*Aspergillus niger*), Amano AK (Pseudomonas sp.), *Pseudomonas fluorescens* lipase (Biocatalyst Ltd.), Amano Lipase P-30 (Pseudomonas sp.), Amano P (*Pseudomonas fluorescens*), Amano AY-30 (*Candida cylindracea*), Amano N (*Rhizopus niveus*), Amano R (Penicillium sp.), Amano FAP (*Rhizopus oryzae*), Amano AP-12 (*Aspergillus niger*), Amano MAP (*Mucor meihei*), Amano GC-4 (*Geotrichum candidum*), Sigma L-0382 and L-3126 (porcine pancrease), Sigma L-3001 (*Wheat germ*), Sigma L-1754 (*Candida cylindracea*), Sigma L-0763 (*Chromobacterium viscosum*) and Amano K-30 (*Aspergillus niger*). Additionally, exemplary enzymes derived from animal tissue include esterase from pig liver, α-chymotrypsin and pancreatin from pancreas such as Porcine Pancreatic Lipase (Sigma). Two or more, as well as a single, enzyme may be employed when carrying out the instant processes.

The preferred embodiments of the instant invention are described further in the following Reaction Schemes. While, for clarity, these Reaction Schemes illustrate the resolution of certain cis enantiomeric mixtures, it is understood that the embodiments as described apply to the resolution of the other enantiomeric mixtures of the present invention as well.

Reaction Scheme I
Resolution by Esterification

Enantiomeric Mixture                Products

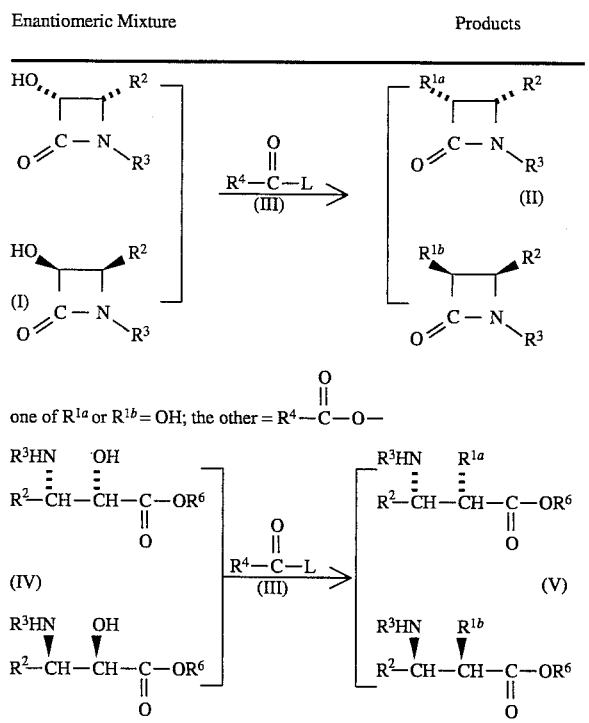

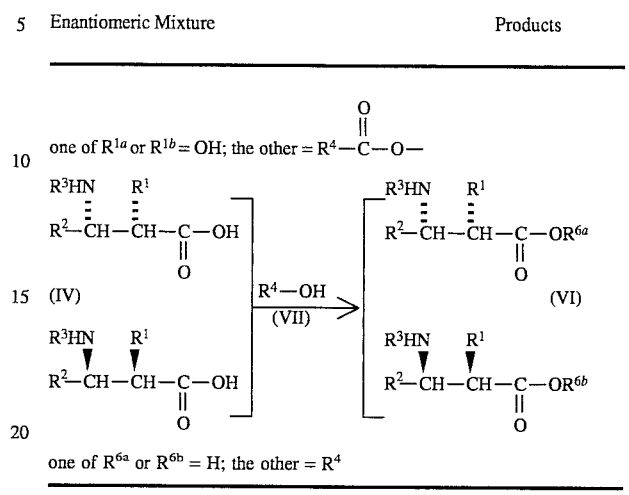

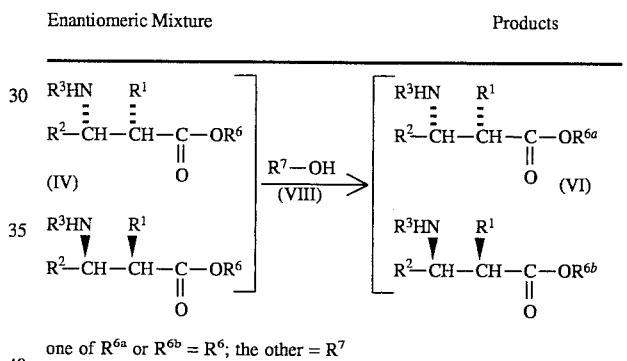

Mixtures I and IV may be selectively esterified as illustrated in the above Reaction Scheme I, and mixture IV may be selectively transesterified as illustrated in the above Reaction Scheme II.

(A) Acylation

Mixture I may be selectively esterified to form mixture II, and mixture IV may be selectively esterified to form mixture V by use of an acylating agent of the formula III:

In formula III, $R^4$ may be an alkyl, alkenyl, alkynyl, aryl, cycloalkyl, cycloalkenyl or hetero group. Preferred $R^4$ groups in formula III are alkyl groups such as $C_{1-6}$ alkyl groups, especially methyl. L is a leaving group which may be displaced to form an ester group. Exemplary L groups include halogen atoms, hydroxyl, alkoxy, or alkenyloxy groups. Preferred L groups are alkenyloxy groups, most preferably $C_{1-6}$ alkenyloxy groups such as $CH_2=CH-O-$ and $CH_2=C(CH_3)-O-$. Any acylation agent of formula III which effects esterification may be employed, with isopropenyl acetate and vinyl acetate being particularly preferred.

(B) Esterification with alcohol

Mixture IV may be selectively esterified to form mixture VI by use of an organic alcohol of the formula VII:

$$R^4\text{—OH} \tag{VII}$$

In formula VII, $R^4$ may be an alkyl, alkenyl, alkynyl, aryl, cycloalkyl, cycloalkenyl or hetero group. Alkyl groups, particularly $C_{1-6}$ alkyl groups, are preferred as $R^4$.

(C) Transesterification with alcohol

Mixture IV may be selectively transesterified to form mixture VI by use of an alcohol of the formula VIII:

$$R^7\text{—OH} \tag{VIII}$$

In formula VIII, $R^7$ may be an alkyl, alkenyl, alkynyl, aryl, cycloalkyl, cycloalkenyl or hetero group, except that $R^7$ is not the same as $R^6$. It is preferred that the group $R^7$ be as distinct as possible from the group $R^6$ to facilitate subsequent separation of the compound bearing the group $R^7$—O—C(O)— from the compound bearing the group $R^6$—O—C(O)—. Thus, it is preferred to employ an alcohol of the formula VIII in which the $R^7$ group differs with respect to the group $R^6$ in terms of molecular weight, or otherwise imparts distinctive physical or chemical properties to the transesterified ester.

The esterification (acylation) procedure (A), and the esterification and transesterification procedures (B) and (C), are preferably carried out in an organic solvent. Exemplary solvents suitable for use in these processes include 1,1,2-trichloro- 1,2,2-trifluoroethane, toluene, cyclohexane, benzene, hexane, heptane, isooctane, octane, methyl ethyl ketone, methyl isobutyl ketone and the like. Water is preferably added to the reaction mixture in small amounts. When present, the concentration of water in the reaction mixture is preferably from about 0.01% to about 1% based on the weight of solvent, or present in a concentration less than or equal to that where the organic solvent is saturated. Water is most preferably present in an amount of about 0.05% to about 0.5% based on the weight of solvent. The reaction solution preferably contains between about 5 to about 250 mg of the enantiomeric starting compounds per ml of solvent.

To carry out these processes, a compound III, VII or VIII is added to the reaction medium. Preferred molar ratios of the compound III: compounds of mixture I or IV are from about 1:1 to about 4:1; preferred molar ratios of the compound VII: compounds of mixture IV are from about 1:1 to about 4:1; and preferred molar ratios of the compound VIII: compounds of mixture IV are from about 1:1 to about 4:1.

The enzymes or microorganisms employed in these procedures are preferably lipases or esterases or microorganisms capable of producing these enzymes. Enzymes or microorganisms particularly preferred in these processes are Lipase P-30 from Pseudomonas sp., Lipase N from *Rhizopus niveus*, Lipase APF from *Aspergillus niger*, Lipase GC-20 from *Geotrichum candidum*, Lipase AK from Pseudomonas sp., Lipase AY-30 from Candida sp., and *Pseudomonas fluorescens* Lipase.

An enzyme may, for example, be used in its free state or in immobilized form. A preferred embodiment of the invention is that where an enzyme is adsorbed onto a suitable carrier, e.g., diatomaceous earth (porous Celite Hyflo Supercel), microporous polypropylene (Enka Accurel® polypropylene powder), or a nonionic polymeric adsorbent such as Amberlite® XAD-2 (polystyrene) or XAD-7 (polyacrylate) from Rohm and Haas Co. When employed to immobilize an enzyme, a carrier may control the enzyme particle size and prevent aggregation of the enzyme particles when used in an organic solvent. Immobilization can be accomplished, for example, by precipitating an aqueous solution of the enzyme with cold acetone in the presence of the Celite Hyflo Supercel followed by vacuum drying, or in the case of a nonionic polymeric adsorbent, incubating enzyme solutions with adsorbent on a shaker, removing excess solution and drying enzyme-adsorbent resins under vacuum. The enzyme is preferably added to the reaction solution to achieve concentrations ranging from about 5 to about 200 mg of enzyme per ml of solvent. While it is desirable to use the least amount of enzyme possible, the amount of enzyme required will vary depending upon the specific activity of the enzyme used.

These processes may also be carried out using microbial cells containing an enzyme having the ability to catalyze the stereoselective conversions. When using a microorganism to perform the resolution, these procedures are conveniently carried out by adding the cells and the enantiomeric mixture starting material to the desired reaction medium. Cells may be used in the form of intact cells, dried cells such as lyophilized, spray-dried or heat-dried cells, immobilized cells, or cells treated with organic solvents such as acetone or toluene. Cells may also be used in the form of treated cell material such as ruptured cells or cell extract. Cell extracts immobilized on Celite® or Accurel® polypropylene as described earlier may also be employed.

Incubation of the reaction medium is preferably at a temperature between about 4 and about 60° C. and is most preferably between about 30 to 50° C. The reaction time can be appropriately varied depending upon the amount of enzyme used and its specific activity. Typical reaction times at 30° C. for optical purities of 98 percent and above are at least about 24 hours and can range up to about 72 hours for greater conversions and higher optical purities, e.g., optical purities exceeding 99.5 percent. Reaction times may be reduced by increasing the reaction temperature and/or increasing the amount of enzyme added to the reaction solution.

Reaction Scheme III
Resolution by Hydrolysis

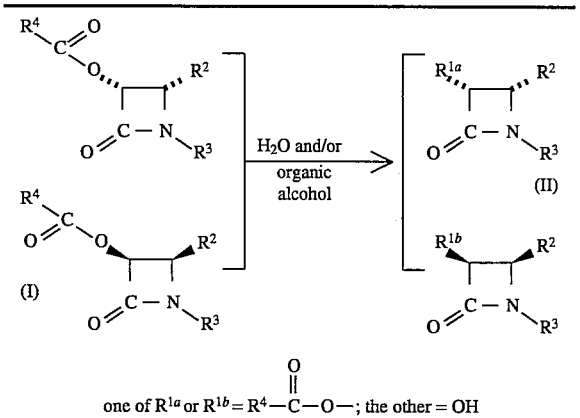

Reaction Scheme III
Resolution by Hydrolysis

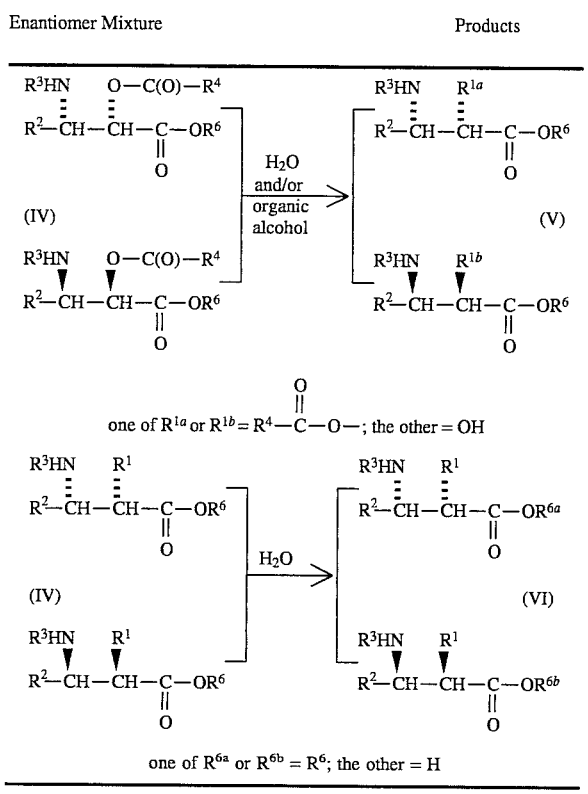

As can be seen from Reaction Scheme III above, mixtures I and IV may be selectively hydrolyzed to form mixtures II and V, respectively, by use of water and/or an organic alcohol, and mixture IV may be selectively hydrolyzed to form mixture VI by use of water. The groups $R^4$, forming part of $R^1$, and $R^6$ in the starting enantiomeric compounds are preferably alkyl, most preferably $C_{1-6}$ alkyl such as methyl.

A compound of the formula IX:

$$R^8-OH \qquad (IX)$$

may be employed as the organic alcohol, where $R^8$ is an alkyl, alkenyl, alkynyl, aryl, cycloalkyl, cycloalkenyl or hetero group, and $R^8$ is preferably alkyl such as methyl. Use of the organic alcohol IX may result in the formation of the by-product ester

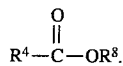

Use of water as the hydrolysis agent may result in the formation of the by-product acid

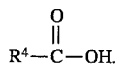

To maintain a steady pH as these acidic by-products are generated, a base such as an alkali metal hydroxide may be added. When an organic alcohol IX is employed, an amount providing a molar ratio of compound IX: compounds of mixtures I or IV of from about 1:1 to about 4:1 is preferably added.

These processes preferably employ water-soluble enzymes capable of catalyzing stereoselective hydrolysis. Especially suitable for use with these processes are lipases and esterases, as well as pancreatin and α-chymotrypsin. Either the crude or purified forms of these enzymes, in free form or immobilized on support, may be employed. Particularly preferred in these processes are Lipase PS-30 from Pseudomonas sp. (*Pseudomonas cepacia*) (Amano Int'l) (preferably free or immobilized on a resin such as XAD-7, XAD-2 or Accurel® resins as described above), Lipase P-30 (Amano) from Pseudomonas sp., Lipase GC-20 Geotrichum candidum (Amano Int'l), Lipase N *Rhizopus niveus* (Amano Int'l), Lipase APF *Aspergillus niger* (Amano Int'l); Lipase AY-30 Candida sp. (Amano), Lipase AK Pseudomonas sp. (Amano Int'l), *Pseudomonas fluorescens* Lipase (Biocatalyst Ltd.) and Porcine Pancreatic Lipase (Sigma Chem).

The above hydrolyses are preferably conducted in an aqueous or buffered aqueous medium or in a biphasic solvent system comprising an organic phase, immiscible in water, and an aqueous phase. Use of a two phase solvent system may enhance the efficiency of such processes where the substrate material is insoluble in water.

Solvents for the organic phase of a biphasic solvent system may be any organic solvent immiscible in water, such as toluene (which is preferred), cyclohexane, xylene, trichlorotrifluoroethane and the like. The aqueous phase is conveniently of water, preferably deionized water, or a suitable aqueous buffer solution, especially a phosphate buffer solution. The biphasic solvent system preferably comprises between about 10 to 90 percent by volume of organic phase and between about 90 to 10 percent by volume of aqueous phase, and most preferably contains at or about 20 percent by volume of organic phase and at or about 80 percent by volume of the aqueous phase.

A particularly preferred reaction system comprises a biphasic solvent system as described above, an amount of enantiomeric mixture starting material of from about 0.1 to about 100 mg per ml of biphasic solvent, and one or more enzymes in an amount of from about 0.1 to about 100 mg enzyme per mg of starting material to be hydrolyzed.

An exemplary embodiment of such processes starts with preparation of an aqueous solution of the enzyme(s) to be used. For example, the preferred enzyme(s) can be added to a suitable amount of an aqueous solvent, such as phosphate buffer or the like. This mixture is preferably adjusted to and maintained at about pH 7.0, preferably with an aqueous alkali metal hydroxide, carbonate or bicarbonate. Centrifugation at reduced temperatures (e.g., 4° C.) is preferably employed to provide the enzyme-containing aqueous portion of the biphasic solvent system. Thereafter, an emulsion of the enantiomeric starting material in an organic solvent and aqueous solvent is formed and cooled. The enantioselective hydrolysis may be effectuated by adding the enzyme-containing aqueous solvent to this emulsion, preferably while continuing agitation and cooling.

The reaction time may vary from enzyme to enzyme but typical reaction times are about 24 to 72 hours, depending on the temperature and the enzyme concentration. Temperatures of from about 4° C. to about 60° C. are preferably employed.

Reaction Scheme IV
Resolution by Dehalogenation

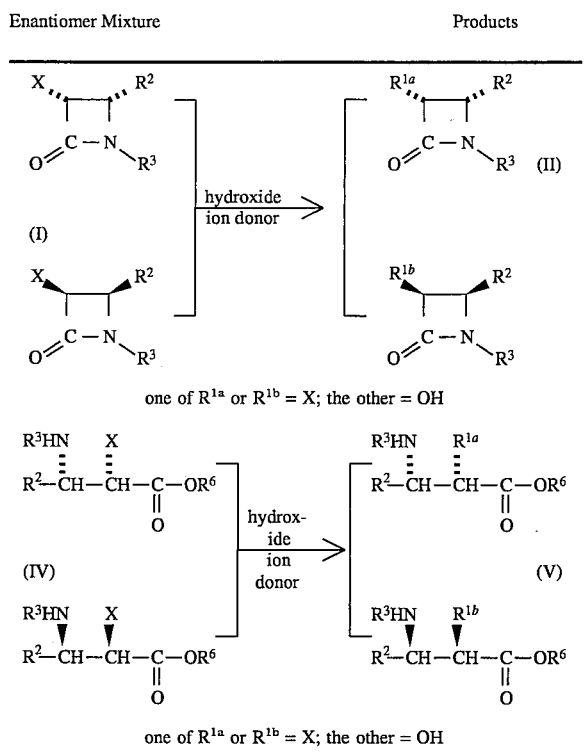

one of $R^{1a}$ or $R^{1b}$ = X; the other = OH one of $R^{1a}$ or $R^{1b}$ = X; the other = OH As can be seen from Reaction Scheme IV above, mixtures I and IV may be selectively dehalogenated to form mixtures II and V, respectively, wherein X denotes a halogen atom.

Any compound capable of effecting these reactions may be employed as the hydroxide ion donor. Exemplary such compounds are selected from water, alkali or alkaline earth metal hydroxides such as sodium and potassium hydroxide, and ammonium hydroxides such as quaternary ammonium hydroxides, for example, those of the formula $(R^9)_4NOH$ where $R^9$ is hydrogen or alkyl, particularly potassium hydroxide and water. Amounts of the hydroxide ion donor added are preferably those providing a molar ratio of hydroxide ion donor: mixture I or IV enantiomeric starting material of from about 1:1 to about 4:1.

A reaction medium containing water and an organic solvent such as toluene or hexane is preferably employed. The enantiomeric starting materials are preferably employed in an amount of from about 1 mg to about 100 mg per ml of solvent.

Enzymes or microorganisms employed in the dehalogenation reaction are preferably selected from the genera Pseudomonas, Trichoderma, Acinetobacter, Alcaligenes, Nocardia, Mycobacterium, Rhodococcus, Methanobacterium, Proteus, or enzymes derived therefrom, and are preferably employed in amounts of from about 0.1 mg to about 10 mg enzyme per mg of starting material to be dehalogenated.

Temperatures of from about 4° C. to about 50° C. are preferably employed.

Separation

The products of the stereoselective conversions may be isolated and purified by known methodologies such as extraction, distillation, crystallization, column chromatography, and the like.

A preferred method for separating the product mixtures formed by the methods of the present invention is by partitioning the undesired and desired compounds of the product mixture between two or more immiscible liquids in which these compounds have different solubilities. The use of water and an immiscible organic liquid is preferred.

Utility

Taxanes are diterpene compounds containing the taxane carbon skeleton:

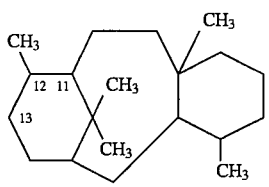

which skeleton may contain ethylenic unsaturation in the ring system thereof. Of particular interest are taxanes having the above carbon skeleton wherein the 11, 12-positions are bonded through an ethylenic linkage, and the 13-position contains a side chain, which taxanes are exemplified by taxol, Pharmacologically active taxanes, such as taxol, may be used as antitumor agents to treat patients suffering from cancers such as ovarian cancer, melanoma, breast, colon or lung cancer, and leukemia.

The resolved compounds obtained by the methods of the present invention are particularly useful as intermediates in forming the aforementioned side chain on the taxane skeleton. The addition of such a side chain, in and of itself, may impart an increased or more desirable pharmacological activity to the taxane product, or may form a taxane product which is more readily converted to a taxane having an increased or more desirable pharmacological activity than the starting compound.

The compounds resolved according to the methods of the present invention may be modified prior to use in side chain formation. For example, resolved compounds containing an azide group $N_3$ as the group W may be treated by a reducing agent to form an amine group which may be substituted.

Exemplary methods for side chain formation, and taxane products which may be formed employing such methods, include those described in U.S. Pat. Nos. 4,924,011, 4,924,012, and European Patent Application No. 400,971, all three documents of which are incorporated herein by reference.

Salts or solvates of reactants or products may be employed or prepared as appropriate or desired in the methods of the present invention.

The methods of the present invention are further described by the following examples. These examples are illustrative only, and are in no way intended to limit the scope of the instant claims.

EXAMPLE 1

Stereoselective hydrolysis of
(±)-cis-3-acetoxy-4-phenyl-2-azetidinone

Substrate: the racemic title compound, that is,

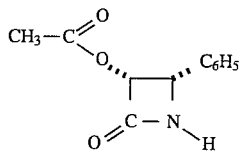

(Ia(1))

and

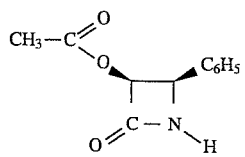

(Ib(1))

Product:
(+)-cis-3-acetoxy-4-phenyl-2-azetidinone

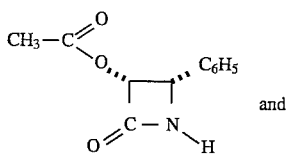

(IIa(1))

and (−)-cis-3-hydroxy-4-phenyl-2-azetidinone

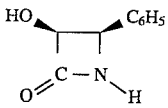

(IIb(1))

A reaction mixture in 1 L of 25 mM potassium phosphate buffer pH 7.0 was prepared containing 8 grams of substrate, 80 grams of lipase PS-30 from Pseudomonas sp. (Amano International Co.). The reaction was carried out at 30° C., 150 revolutions-per-minute (RPM) agitation. During the reaction, the pH of the reaction mixture was maintained at 7.0 with 5N NaOH using a pH stat. The hydrolysis reaction was monitored by high pressure liquid chromatography. Periodically, samples (1 ml) were taken and extracted with 4 ml of ethyl acetate. The ethyl acetate layer was separated and evaporated to dryness and analyzed by HPLC for the substrate and product concentration and the optical purity of the product. The results obtained are as shown in the following Table 1.

TABLE 1

| Reaction Time (Hours) | Conversion (% product IIb) | Yield (% product IIa) | Optical purity of product IIa (%) |
|---|---|---|---|
| 24 | 13.5 | 86.5 | — |
| 48 | 28.0 | 72.0 | — |
| 72 | 40.0 | 60.0 | — |
| 96 | 51.0 | 49.0 | >99.6 |

A mixture II wherein $R^2$ is phenyl, $R^3$ is hydrogen, $R^{1a}$ is acetyloxy and $R^{1b}$ is hydroxyl, such as that prepared above, may be separated by partitioning, as the compound IIb has a greater aqueous solubility than the compound IIa. A particularly preferred procedure for the separation of these compounds from an aqueous mixture is as follows: (1) extraction with ethyl acetate; and (2) separation of the organic layer and addition of heptane thereto to form an ethyl acetate:heptane mixture (1:1 by volume), followed by two washings with water (1:1 by volume, $H_2O$:ethyl acetate/heptane each). The organic layers obtained from (2) preferably contain the compound IIa and none of the compound IIb. Further separation of these compounds from the aqueous layers, which may still contain small amounts of compound IIa, may be achieved by additional ethyl acetate/heptane extractions followed by aqueous (such as 5–10% w/w NaCl, aqueous or water only) washings.

EXAMPLE 2

Stereoselective hydrolysis of
(±)-1-(4-methoxyphenyl)-cis-3-acetoxy-4-phenyl-2-azetidinone Substrate: the racemic title compound, that is,

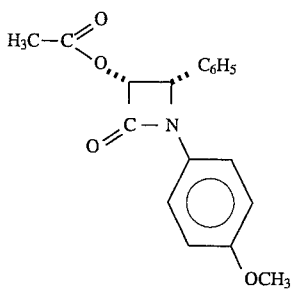

(Ia(1))

and

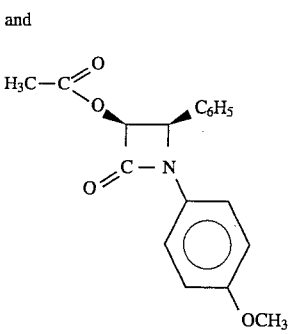

(Ib(1))

Product

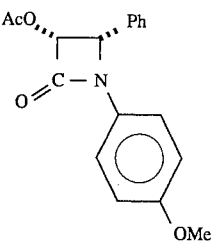

(IIa(1))

and

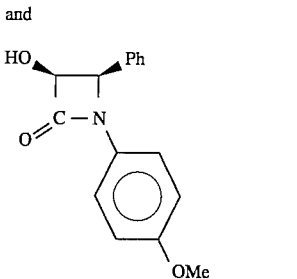

(IIb(1))

A reaction mixture in 1 L of 25 mM potassium phosphate buffer pH 7.0 was prepared containing 5 grams of substrate, 50 grams of lipase PS-30 from Pseudomonas sp. (Amano International Co.). The reaction was carried out at 30° C., 150 RPM agitation. During the reaction, the pH of the reaction mixture was maintained at 7.0 with 5N NaOH using a pH stat. The hydrolysis reaction was monitored by high pressure liquid chromatography. Periodically, samples (1 ml) were taken and extracted with 4 ml of ethyl acetate. The ethyl acetate layer was separated and evaporated to dryness and analyzed by HPLC for the substrate and product concentration and the optical purity of the product. The results obtained are as shown in the following Table 2.

TABLE 2

| Reaction Time (Hours) | Conversion (% product IIb) | Yield (% product IIa) | Optical purity of product IIa (%) |
|---|---|---|---|
| 24 | 12 | 88 | — |
| 48 | 36 | 64 | — |
| 72 | 43 | 57 | — |
| 96 | 52 | 48 | >99.7 |

EXAMPLE 3

Stereoselective hydrolysis of (±)-cis-3-acetoxy-4-phenyl-2-azetidinone using immobilized enzyme The substrate employed, and product provided, were those of Example 1 above.

Immobilization of Enzyme

Three different carriers—XAD-7 (Amberlite XAD-7 nonionic polymeric adsorbent, 20–60 mesh polyacrylate resin), XAD-2 (Amberlite XAD-nonionic polymeric adsorbent, 20–60 mesh polystyrene resin) and Accurel PP (polypropylene resin 200–400 microns)—were used for the immobilization procedures.

Crude Amano PS-30 lipase (10 g) was dissolved in 25 ml of distilled water and centrifuged at 10,000 RPM for 10 minutes to obtain clear supernatant. The carrier (1.3 g) in a 25 ml vial was washed 5 times with methanol and added to enzyme solution in a flask and gently agitated on a gyrotory shaker at room temperature. Adsorption of enzyme to the carrier was checked periodically by lipase assay (Sigma olive oil emulsion as substrate) and by protein remaining in filtrate. About 68%, 71% and 98% adsorption efficiencies were obtained using XAD-7, XAD-2, and Accurel resins, respectively. After complete immobilization (20 to 24 hours), the carrier-enzyme slurry was filtered through a Millipore filter and the carrier was washed with about 300 ml of distilled water. Subsequently, the carrier containing the immobilized lipase was dried in a vacuum oven at room temperature.

Use of Immobilized Enzyme

Immobilized enzyme was evaluated for the enzymatic hydrolysis reaction described in Example 1. Reaction mixtures were prepared in 20 ml volume containers (18 ml of 25 mM potassium phosphate buffer pH 7.0 and 2 ml of toluene), containing 200 mg of substrate as described in Example 1, and 200 mg of the above prepared immobilized Lipase PS-30. The reactions were conducted as described in Example 1. The results obtained are shown in the following Table 3.

TABLE 3

Evaluation of Immobilized Enzyme on the Stereoselective Hydrolysis Reaction

| Immobilized Support | Reaction Time (Hours) | Conversion (% product IIb) | Yield (% product IIa) | % Optical purity of product IIa |
|---|---|---|---|---|
| XAD-2 | 72 | 52 | 48 | >99.5 |
| XAD-7 | 72 | 53 | 47 | >99.5 |
| Accurel PP | 72 | 51 | 49 | >99.5 |

EXAMPLE 4

Stereoselective hydrolysis of (±)-cis-3-acetoxy-4-phenyl-2-azetidinone: varying the lipase employed The substrate employed, and product provided, were those of Example 1 above. In this example, a number of reactions were run in which lipases from different sources were employed.

In each reaction, the reaction mixture, in 20 ml of 25 mM phosphate buffer, pH 7.0, contained 1 gram of crude lipase and 50 mg of substrate. The reactions were conducted at 25° C. in a pH stat at pH 7.0. The results obtained are shown in the following Table 4.

TABLE 4

| Enzyme | Source | Conversion (%) IIb | Yield (%) IIa | Optical Purity (%) IIa |
|---|---|---|---|---|
| Lipase P-30 Pseudomonas sp. | Amano Int. | 69 | 31 | >99.5 |
| Lipase GC20 Geotrichum candidum | Amano Int. | 60 | 40 | 100 |
| Lipase N Rhizopus niveus | Amano Int. | 70 | 30 | >99.5 |
| Lipase APF Aspergillus niger | Amano Int. | 80 | 20 | >99.5 |
| Lipase AY-30 Candida sp. | Amano Int. | 65 | 35 | 100 |
| Lipase AK Pseudomonas sp. | Amano Int. | 63 | 37 | 100 |
| Pseudomonas fluorescens Lipase | Biocatalyst Ltd. | 64 | 36 | >99.5 |
| Porcine Pancreatic Lipase | Sigma Chem. | 65 | 35 | 99.0 |

EXAMPLE 5

Stereoselective acetylation (esterification) of (±)-cis-3-hydroxy-4-phenyl-2-azetidinone Substrate: the racemic title compound, that is,

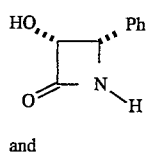 (Ia(1))

and

-continued (Ib(1))

[Structure: HO and Ph on azetidinone ring with NH]

Product:
(−)-cis-3-acetoxy-4-phenyl-2-azetidinone (IIb(1))

[Structure: AcO and Ph on azetidinone ring with NH]

(+)-cis-3-hydroxy-4-phenyl-2-azetidinone (IIa(1))

[Structure: HO and Ph on azetidinone ring with NH]

In this example, a number of reactions were run in which lipases from different sources were employed.

In each reaction, the reaction mixture, in ml of toluene contained 1 gram of crude lipase and 100 mg of substrate, 800 mg of isopropenyl acetate, and 0.05% water. The reactions were conducted at 30° C. and 100 RPM on a shaker. The products and substrates were analyzed by HPLC. The results are shown on the following Table 5.

TABLE 5

| Enzyme* | Source | Conversion (%) IIa | Optical Purity (%) IIa |
|---|---|---|---|
| Lipase P-30 | Amano Int. | 48 | >99.2 |
| Lipase GC-20 | Amano Int. | 42 | >99.1 |
| Lipase AY-30 | Amano Int. | 36 | >98.0 |
| Lipase N | Amano Int. | 32 | >98.5 |

*See Table 4 above for microorganism source.

What is claimed is:

1. A method for the resolution of a mixture I comprising the enantiomers Ia and Ib, where $R^1$ is in the cis position relative to $R^2$ in both Ia and Ib:

(Ia)

[Azetidinone structure with $R^1$, $R^2$, $R^3$]

(Ib)

[Azetidinone structure with $R^1$, $R^2$, $R^3$]

to form a mixture II comprising the compounds IIa and IIb, where $R^{1a}$ and $R^{1b}$ are in the cis position relative to $R^2$ in both IIa and IIb:

(IIa)

[Azetidinone structure with $R^{1a}$, $R^2$, $R^3$]

(IIb)

[Azetidinone structure with $R^{1b}$, $R^2$, $R^3$]

where $R^1$ is —O—C(O)-alkyl or —O—C(O)-alkenyl;

one of $R^{1a}$ or $R^{1b}$ is the same as $R^1$ and the other of $R^{1a}$ or $R^{1b}$ is hydroxyl;

$R^2$ is aryl; and $R^3$ is hydrogen, aryl, —C(O)—O-alkyl, or —C(O)-aryl;
wherein said alkyl and alkenyl groups contain 1 to 15 carbons in the normal chain and said aryl groups contain 6 to 12 carbons in the ring portion;
comprising the steps of (a) contacting said mixture I with a carboxylic ester hydrolase enzyme or a microorganism having a carboxylic ester hydrolase enzyme, wherein said enzyme catalyzes the stereoselective hydrolysis of said mixture I to provide said mixture II, (b) effecting said hydrolysis, and (c) recovering one or both of said compounds IIa and IIb.

2. The method of claim 1, wherein said mixture I is resolved in contact with water and/or an organic alcohol to form said mixture II.

3. The method of claim 2, wherein, in said mixture I:

$R^1$ is alkanoyloxy;

$R^2$ is phenyl or substituted phenyl; and $R^3$ is hydrogen, phenyl, substituted phenyl, phenylcarbonyl, substituted phenycarbonyl, or tert-butoxycarbonyl, wherein substituted phenyl denotes phenyl substituted by halogen, hydroxyl or alkoxy.

4. The method of claim 3, wherein said mixture I comprises (±)-cis- 3-acetoxy-4-phenyl-2-azetidinone and said mixture II comprises the compound IIa(1) which has the structure:

[Structure: $H_3C$-C(=O)-O on azetidinone with phenyl and NH]

and the compound IIb(1) which has the structure:

[Structure: HO on azetidinone with phenyl and N=O]

5. The method of claim 3, wherein said mixture I comprises (±)-1-( 4-methoxyphenyl)-cis-3-acetoxy-4-phenyl-2-azetidinone and said mixture II comprises the compound IIa(1) which has the structure:

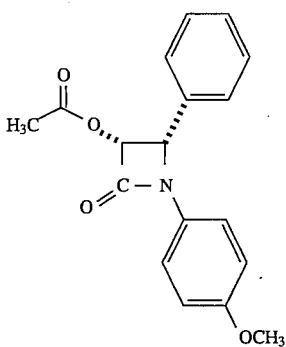

and the compound IIb(1) which has the structure:

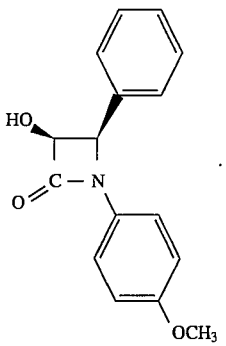

6. The method of claim 1, wherein said enzyme is an esterase, lipase or protease.

7. The method of claim 6, wherein said enzyme is a lipase.

8. The method of claim 7, wherein said lipase is selected from the group consisting of lipase PS-30 from Pseudomonas sp., lipase P-30 from Pseudomonas sp., lipase GC-20 from *Geotrichum candidum*, lipase N from *Rhizopus niveus*, lipase APF from *Aspergillus niger*, lipase AY-30 from Candida sp., lipase AK from Pseudomonas sp., *Pseudomonas fluorescens* lipase and porcine pancreatic lipase.

9. The method of claim 1, wherein said enzyme is immobilized on a support.

10. A method for the resolution of a mixture I comprising the enantiomers Ia and Ib, where $R^1$ is in the trans position relative to $R^2$ in both Ia and Ib:

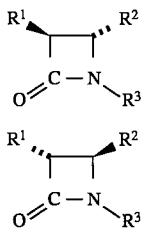

to form a mixture II comprising the compounds IIa and IIb, where $R^{1a}$ and $R^{1b}$ are in the trans position relative to $R^2$ in both IIa and IIb:

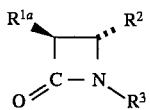

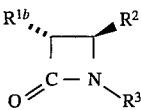

where $R^1$ is —O—C(O)-alkyl or —O—C(O)-alkenyl;

one of $R^{1a}$ or $R^{1b}$ is the same as $R^1$ and the other of $R^{1a}$ or $R^{1b}$ is hydroxyl;

$R^2$ is aryl; and $R^3$ is hydrogen, aryl, —C(O)—O-alkyl, or —C(O)-aryl;

wherein said alkyl and alkenyl groups contain 1 to 15 carbons in the normal chain and said aryl groups contain 6 to 12 carbons in the ring portion;

comprising the steps of (a) contacting said mixture I with a carboxylic ester hydrolase enzyme or a microorganism having a carboxylic ester hydrolase enzyme, wherein said enzyme catalyzes the stereoselective hydrolysis of said mixture I to provide said mixture II, (b) effecting said hydrolysis, and (c) recovering one or both of said compounds IIa and IIb.

11. The method of claim 10, wherein said mixture I is resolved in contact with water and/or an organic alcohol to form said mixture II.

12. The method of claim 11, wherein, in said mixture I:

$R^1$ is alkanoyloxy;

$R^2$ is phenyl or substituted phenyl; and $R^3$ is hydrogen, phenyl, substituted phenyl, phenylcarbonyl, substituted phenycarbonyl, or tert-butoxycarbonyl, wherein substituted phenyl denotes phenyl substituted by halogen, hydroxyl or alkoxy.

13. The method of claim 10, wherein said enzyme is an esterase, lipase or protease.

14. The method of claim 13, wherein said enzyme is a lipase.

15. The method of claim 14, wherein said lipase is selected from the group consisting of lipase PS-30 from Pseudomonas sp., lipase P-30 from Pseudomonas sp., lipase GC-20 from *Geotrichurn candidum*, lipase N from *Rhizopus niveus*, lipase APF from *Aspergillus niger*, lipase AY-30 from Candida sp., lipase AK from Pseudomonas sp., *Pseudomonas fluorescens* lipase and porcine pancreatic lipase.

16. The method of claim 10, wherein said enzyme is immobilized on a support.

17. A method for the resolution of a mixture I comprising the enantiomers Ia and Ib, where $R^1$ is in the cis position relative to $R^2$ in both Ia and Ib:

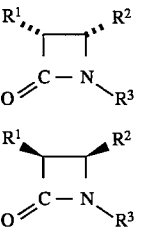

to form a mixture II comprising the compounds IIa and IIb, where $R^{1a}$ and $R^{1b}$ are in the cis position relative to $R^2$ in both IIa and IIb:

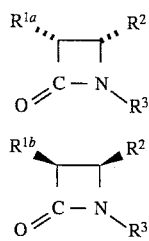

(IIa)

(IIb)

where $R^1$ is hydroxyl;

one of $R^{1a}$ or $R^{1b}$ is hydroxyl and the other of $R^{1a}$ or $R^{1b}$ is —O—C(O)-alkyl or —O—C(O)-alkenyl;

$R^2$ is aryl; and $R^3$ is hydrogen, aryl, —C(O)—O-alkyl, or —C(O)-aryl;

wherein said alkyl and alkenyl groups contain 1 to 15 carbons in the normal chain and said aryl groups contain 6 to 12 carbons in the ring portion;

comprising the steps of (a) contacting said mixture I with a compound III:

where $R^4$ is alkyl or alkenyl and L is a leaving group, and with a carboxylic ester hydrolase enzyme or a microorganism having a carboxylic ester hydrolase enzyme, wherein said enzyme catalyzes the stereoselective esterification of said mixture I to provide said mixture II, (b) effecting said esterification, and (c) recovering one or both of said compounds IIa and IIb.

18. The method of claim 17, wherein, in said mixture II:

$R^{1a}$ or $R^{1b}$ is alkanoyloxy;

$R^2$ is phenyl or substituted phenyl; and $R^3$ is hydrogen, phenyl, substituted phenyl, phenylcarbonyl, substituted phenycarbonyl, or tert-butoxycarbonyl, wherein substituted phenyl denotes phenyl substituted by halogen, hydroxyl or alkoxy.

19. The method of claim 17, wherein, in said compound III, L is a halogen atom, hydroxyl, alkoxy or alkenyloxy group.

20. The method of claim 19, wherein said compound III is isopropenyl acetate.

21. The method of claim 18, wherein said mixture I comprises (±)-cis- 3-hydroxy-4-phenyl-2-azetidinone and said mixture II comprises a compound IIa(1) which has the structure:

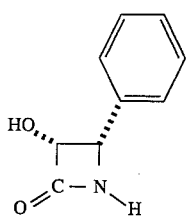

and a compound IIb(1) which has the structure:

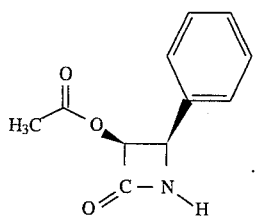

22. The method of claim 17, wherein said enzyme is a lipase.

23. The method of claim 22, wherein said lipase is selected from the group consisting of lipase P-30 from Pseudomonas sp., lipase GC-20 from *Geotrichum candidum*, lipase AY-30 from Candida sp., and lipase N from *Rhizopus niveus*.

24. The method of claim 17, wherein said enzyme is immobilized on a support.

25. A method for the resolution of a mixture I comprising the enantiomers Ia and Ib, where $R^1$ is in the trans position relative to $R^2$ in both Ia and Ib:

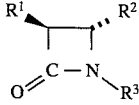  (Ia)

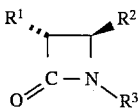  (Ib)

to form a mixture II comprising the compounds IIa and IIb, where $R^{1a}$ and $R^{1b}$ are in the trans position relative to $R^2$ in both IIa and IIb:

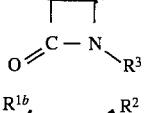  (IIa)

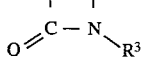  (IIb)

where $R^1$ is hydroxyl;

one of $R^{1a}$ or $R^{1b}$ is hydroxyl and the other of $R^{1a}$ or $R^{1b}$ is —O—C(O)-alkyl or —O—C(O)-alkenyl;

$R^2$ is aryl; and $R^3$ is hydrogen, aryl, —C(O)—O-alkyl, or —C(O)-aryl;

wherein said alkyl and alkenyl groups contain 1 to 15 carbons in the normal chain and said aryl groups contain 6 to 12 carbons in the ring portion;

comprising the steps of (a) contacting said mixture I with a compound III:

where $R^4$ is alkyl or alkenyl and L is a leaving group, and with a carboxylic ester hydrolase enzyme or a microorganism having a carboxylic ester hydrolase enzyme, wherein said enzyme catalyzes the stereoselective esterification of said mixture I to provide said mixture II, (b) effecting said esterification, and (c) recovering one or both of said compounds IIa and IIb.

26. The method of claim 25, wherein, in said mixture II:
$R^{1a}$ or $R^{1b}$ is alkanoyloxy;
$R^2$ is phenyl or substituted phenyl; and
$R^3$ is hydrogen, phenyl, substituted phenyl, phenylcarbonyl, substituted phenycarbonyl, or tert-butoxycarbonyl,
wherein substituted phenyl denotes phenyl substituted by halogen, hydroxyl or alkoxy.

27. The method of claim 25, wherein, in said compound III, L is a halogen atom, hydroxyl, alkoxy or alkenyloxy group.

28. The method of claim 27, wherein said compound III is isopropenyl acetate.

29. The method of claim 25, wherein said enzyme is a lipase.

30. The method of claim 29, wherein said lipase is selected from the group consisting of lipase P-30 from Pseudomonas sp., lipase GC-20 from *Geotrichum candidum*, lipase AY-30 from Candida sp., and lipase N from *Rhizopus niveus*.

31. The method of claim 25, wherein said enzyme is immobilized on a support.

* * * * *